United States Patent [19]

Yamada et al.

[11] Patent Number: 5,762,771
[45] Date of Patent: Jun. 9, 1998

[54] AIR-FUEL RATIO SENSOR

[75] Inventors: Hirokazu Yamada, Nagoya; Takashi Kojima, Kasugai; Toshimi Miyamoto, Okazaki; Koji Shiozawa, Kariya; Makoto Hori, Oogaki; Masahiro Hamaya, Anjo; Minoru Ohta, Okazaki, all of Japan

[73] Assignee: Denso Corporation, Kariya, Japan

[21] Appl. No.: 796,888

[22] Filed: Feb. 6, 1997

[30] Foreign Application Priority Data

Feb. 6, 1996 [JP] Japan .................. 8-045438
Feb. 15, 1996 [JP] Japan .................. 8-054277

[51] Int. Cl.$^6$ .................................. G01N 27/407
[52] U.S. Cl. ............................. 204/428; 204/427
[58] Field of Search .......................... 204/421–429

[56] References Cited

U.S. PATENT DOCUMENTS

| | | | |
|---|---|---|---|
| 4,040,930 | 8/1977 | Dillon | 204/429 |
| 4,116,797 | 9/1978 | Akatsuka | 204/428 |
| 4,569,748 | 2/1986 | Yamakawa et al. | 204/428 |
| 4,683,049 | 7/1987 | Nakajima et al. | 204/428 |
| 4,915,815 | 4/1990 | Shibata et al. | 204/429 |
| 5,073,247 | 12/1991 | Weyl | 204/428 |
| 5,238,552 | 8/1993 | Kato et al. | |

FOREIGN PATENT DOCUMENTS

| | | |
|---|---|---|
| 57-34443 | 7/1982 | Japan . |
| 5-26842 | 2/1993 | Japan . |
| 5-249069 | 9/1993 | Japan . |
| 6-32616 | 8/1994 | Japan . |

*Primary Examiner*—T. Tung
*Attorney, Agent, or Firm*—Cushman Darby & Cushman IP Group of Pillsbury Madison & Sutro LLP

[57] ABSTRACT

An air-fuel ratio sensor comprises an oxygen concentration sensing element, a housing for holding this oxygen concentration sensing element, and protecting covers with gas holes. The protecting covers comprises an inside cover disposed closely to the oxygen concentration sensing element, and an outside cover surrounding the outside cover. Flange-like peripheral portions, formed on the protecting covers, are fixed to the abutting face of the housing by a caulking operation. These flange-like peripheral portions are disposed alternately along a same closed curve around the oxygen concentration sensing element, so that they are not overlapped with each other.

18 Claims, 14 Drawing Sheets

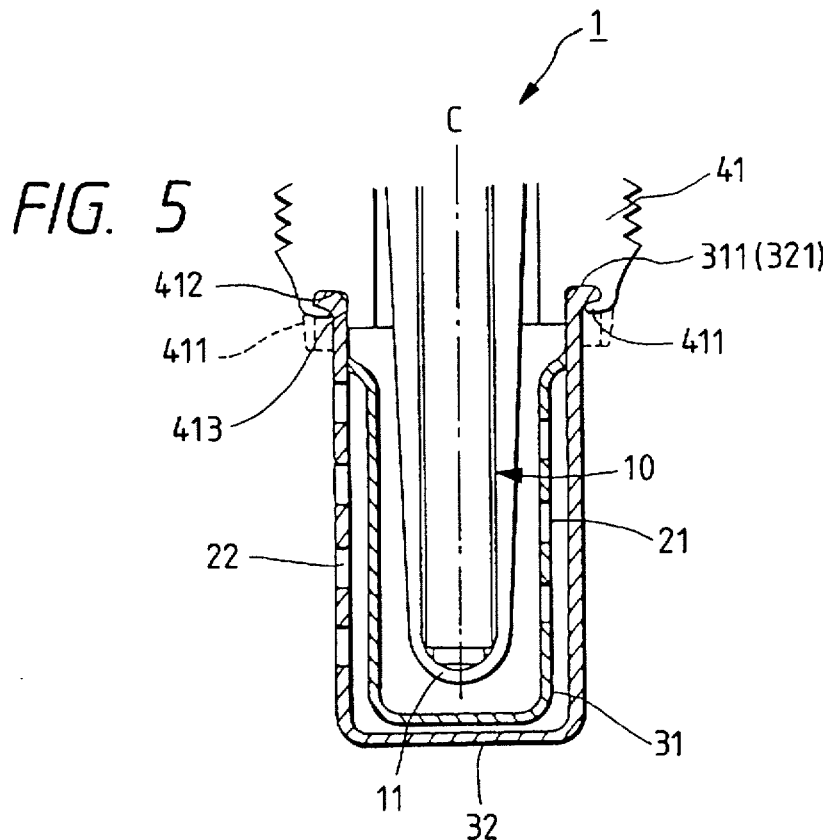
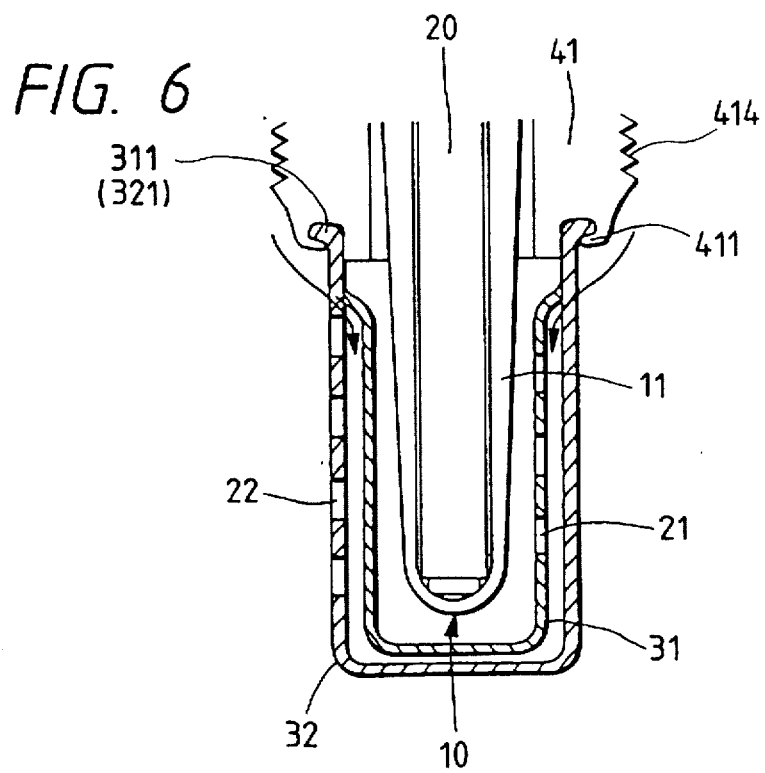

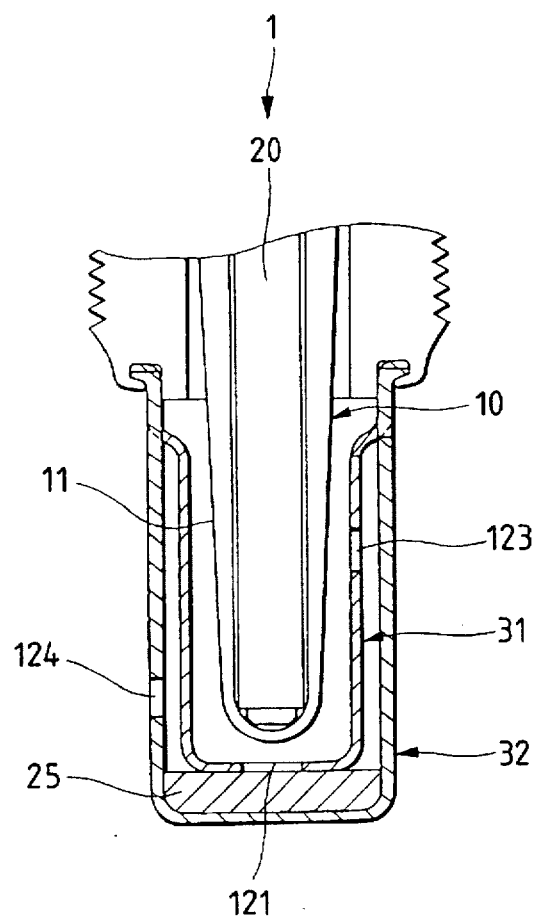
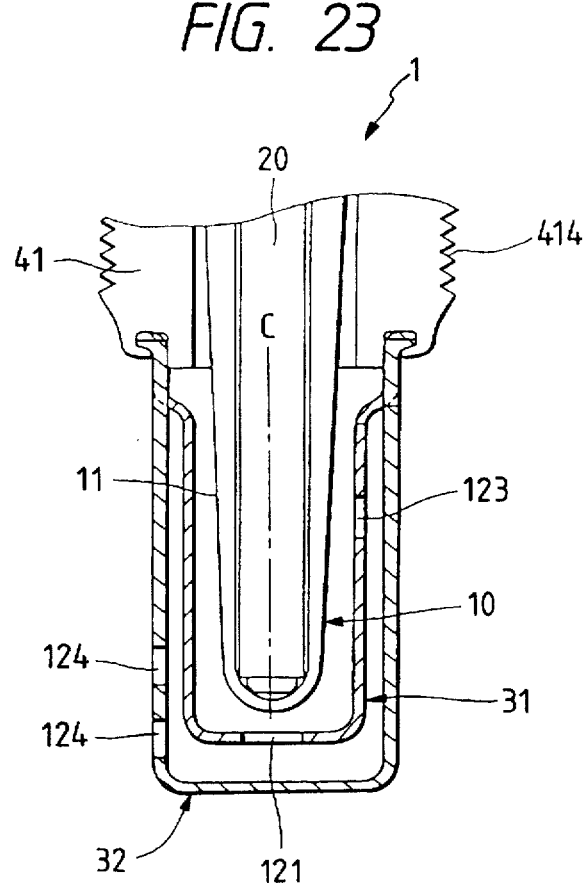

AIR-FUEL RATIO SENSOR

BACKGROUND OF THE INVENTION

1. Field of the Invention

This invention relates to an air-fuel ratio (e.g., oxygen concentration) sensor provided in an exhaust passage for an internal combustion engine of an automotive vehicle or the like, and more particularly to an arrangement of protecting covers covering an air-fuel ratio sensing element, which is simple in installation and reliable against condensed water.

2. Related Art

Gas concentration detectors are incorporated in many of recent internal combustion engines for automotive vehicles to detect and feedback control the air-fuel ratio of gas mixture introduced into their combustion chambers. The air-fuel ratio, detected by a gas concentration detector, is generally used to control the combustion of air/fuel mixture in the combustion chamber to save energy (fuel economy) and emit exhaust gas suitable for attaining an optimum gas purification efficiency in the exhaust gas system comprising a catalytic converter.

An ordinary air-fuel ratio sensor is an electrochemical cell comprising an oxygen-ionic conductive solid electrolyte, such as $ZrO_2$, on the inner and outer wall surfaces of which at least a pair of electrodes and a gas anti-diffusion layer are usually attached. A heater unit is disposed inside the solid electrolyte to warm up the solid electrolyte body to stabilize the output signal of the sensor even in low-temperature conditions, including an engine idling condition and an engine start-up condition.

As shown in FIG. 27, an oxygen sensor 90 comprises a cup-shaped oxygen concentration sensing element 91 constituting an electrochemical cell, and a casing 92 accommodating this oxygen concentration sensing element 91.

The casing 92 comprises a cylindrical housing 93 supporting oxygen concentration sensing element 91 therein. A circumferential flange 931 is provided at a central portion of the cylindrical housing 93, for fixing the sensor body to predetermined portion of an exhaust gas passage of an internal combustion engine. The tip-end portion below the flange 931 is inserted into the exhaust gas passage to expose a closed-end portion of the oxygen concentration sensing element 91 to the exhaust gas. Talc 932 is accumulated between the oxygen concentration sensing element 91 and housing 93, so that the oxygen concentration sensing element 91 is firmly fixed to the housing 93 via talc 932.

Furthermore, a heater unit 96 is inserted inside oxygen concentration sensing element 91. The heater unit 96 is supported to the oxygen concentration sensing element 91 by a holder 961 at an open-end portion of oxygen concentration sensing element 91. The oxygen concentration sensing element 91 comprises a cup-shaped solid electrolyte having one end closed and the other end opened, with an internal electrode and an external electrode formed on the inner and outer wall surfaces thereof. The internal and external electrodes of oxygen concentration sensing element 91 are connected to signal leads 97. The heater unit 96 is connected to a power supply lead 972.

A pair of inside and outside protecting covers 941 and 942, overlapped with each other, are attached to the tip-end portion of the housing 93, so as to cover the closed-end portion of oxygen concentration sensing element 91. Atmospheric covers 951, 952 and 953 sequentially provided at an opposed end (base end) of the housing 93. Protecting covers 941 and 942 cooperatively define an exhaust gas chamber around oxygen concentration sensing element 91. Numerous gas holes 943 and 944 are opened on the walls of these protecting covers 941 and 942, for introducing exhaust gas into the gas chamber. Numerous air holes 954 and 955 are provided on the atmospheric covers 952 and 953, for introducing air into an atmospheric chamber (not shown) formed inside the electrolyte.

A first fixing method for fixing protecting covers 941 and 942 to housing 93 is disclosed in Unexamined Japanese Patent Application No. 5-249069, published in 1993. According to this first fixing method, protecting covers 941 and 942 are welded with each other at their bottoms beforehand and either protecting cover is fixed to the housing 93 by a caulking operation, as shown in FIG. 13.

A second method for fixing the protecting covers to the housing is disclosed in Japanese Utility Model No. 57-34443, published in 1982. According to this second fixing method, the protecting covers are welded with each other at their bottoms beforehand and either protecting cover is welded to the housing.

A third fixing method for fixing the protecting covers to the housing is disclosed in Unexamined Japanese Patent Application No. 5-26842, published in 1993. According to this third fixing method, the protecting covers are separately or independently welded to the housing. All of the above-described first to third methods are common in using a welding operation.

A fourth fixing method, as a method not relying on a welding operation, is disclosed in Japanese Utility Model No. 6-32616, published in 1994. According to this fourth method, a bent portion (skirt portion) having a U-shaped cross section is formed along each cylindrical open-end portion of inside and outside protecting covers having substantially the same diameters. These inside and outside protecting covers are telescopically coupled at their bent portions, so as to constitute a double cover structure. The bent portion of each protecting cover is fixed to the housing by a caulking operation, while a ring is inserted in a hollow space remaining inside the U-shaped bent portion. This ring not only prevents the bent portion from being deformed but provides an airtight sealing structure.

However, according to the above-described first to fourth fixing methods, there are following problems.

The first to third fixing methods are basically based on a welding operation for fixing protecting covers or fixing either protecting cover to the housing. Hence, these methods encounter with the following problems.

First, to guarantee manufacturing qualities at the welded portion, it is generally necessary to finely control the voltage and the current for a resistance welding operation as well as a welding time. In addition, it is necessary to control a pressing force applied to the welded portion during the welding operation. Thus, the manufacturing processes become complicated.

Second, there is a tendency that the oxygen concentration sensing element is cracked when it is subjected to high temperature during the welding operation.

Third, according to the first and second fixing methods, it is difficult to form gas holes at the bottom surface because the inside and outside protecting covers are welded at their bottoms. Thus, it is necessary to provide most of gas holes on the side walls of the inside and outside protecting covers.

On the other hand, according to the fourth fixing method, the inside and outside protecting covers are independently or separately fixed to the housing. Thus, the inside and outside protecting covers need to be fabricated by an accurate machining operation to fit them with each other at their U-shaped bent surfaces (skirt portions) so as to be telescopically coupled smoothly and fixed to the housing surely. Thus, there is a first problem that a high accuracy is required in the machining process of the U-shaped bent portions.

Furthermore, there is a necessity of inserting the ring in a vacant space inside the U-shaped bent portion. Thus, there is a second problem that the number of parts is increased.

Moreover, there is third problem that a large pressing force is required in a caulking operation for fixing the overlapped bent portions of the protecting covers to the housing.

On the other hand, the protecting covers 941 and 942 are provided with gas holes 943 and 944 on their cylindrical walls. For improving the response of the sensor, it is required in these gas holes 943 and 944 that exhaust gas can be quickly introduced to the oxygen concentration sensing element 91. Meanwhile, it is important to protect the oxygen concentration sensing element 91 from condensed water settling in an exhaust gas passage. If the condensed water attaches on the surface of the oxygen concentration sensing element 91, the characteristics of the sensor will be worsened and the heated sensing element 91 may be cracked by a thermal stress due to low-temperature water.

SUMMARY OF THE INVENTION

Accordingly, in view of above-described problems encountered in the related art, a principal object of the present invention is to provide an air-fuel ratio (i.e., oxygen concentration) sensor having protecting covers which are simple in construction, excellent in rigidity, easy to install to a housing, and reliable against condensed water.

In order to accomplish this and other related objects, the present invention provides an air-fuel ratio sensor comprising an air-fuel ratio sensing element with a solid electrolyte having a detecting portion for detecting a gas concentration of measured gas, a housing for holding the air-fuel ratio sensing element, and protecting means for covering the detecting portion of the solid electrolyte, the protecting means having gas holes opened for introducing measured gas. The protecting means of the present invention comprises an inside protecting cover disposed closely to the solid electrolyte and an outside protecting cover surrounding the inside protecting cover. The inside protecting cover is formed into a cup-shaped cylindrical configuration having a closed-end portion at one end and an opened-end portion at the other end. At least one flange-like peripheral portion protruding outward is formed at the opened-end portion of the inside protecting cover. The outside protecting cover is formed into a cup-shaped cylindrical configuration having a closed-end portion at one end and an opened-end portion at the other end. At least one flange-like peripheral portion protruding outward is formed at the opened-end portion of the outside protecting cover. The flange-like peripheral portion of the inside protecting cover and the flange-like peripheral portion of the outside protecting cover are fixed to the housing by a caulking operation.

According to features of preferred embodiments of the present invention, it is preferable that the flange-like peripheral portion of the inside protecting cover and the flange-like peripheral portion of the outside protecting cover are positioned along a same closed curve. The inside protecting cover comprises a plurality of flange-like peripheral portions while the outside protecting cover comprises a plurality of flange-like peripheral portions. The flange-like peripheral portions of the inside protecting cover and the flange-like peripheral portions of the outside protecting cover are alternately positioned along a same closed curve surrounding an axis of the air-fuel ratio sensing element.

Furthermore, at least one cutout portion is formed at the opened-end portion of the outside protecting cover. This cutout portion extends in an axial direction of the outside protecting cover. An expanded connecting portion is formed at the opened-end portion of the inside protecting cover. The expanded connecting portion is coupled with the cutout portion of the outside protecting cover. The flange-like peripheral portion of the inside protecting cover is connected integrally to a distal end of the expanded connecting portion. The flange-like peripheral portion of the inside protecting cover and the flange-like peripheral portion of the outside protecting cover are positioned along a same closed curve when the inside protecting cover is coupled with the outside protecting cover.

Moreover, a clearance is formed between the expanded connecting portion of the inside protecting cover and the cutout of the outside protecting cover when the inside protecting cover is coupled with the outside protecting cover. At least one gas hole is formed on the closed-end portions of the inside and outside protecting covers.

More specifically, the inside protecting cover comprises a cylindrical barrel portion with a closed-end portion at one end and an opened-end portion at the other end, expanded connecting portions being offset radially outward from the open-end portion of the barrel portion, and flange-like peripheral portions integrally formed with the expanded connecting portions so as to protrude outward. The outside protecting cover comprises a cylindrical barrel portion with a closed-end portion at one end and an opened-end portion at the other end, belt-like connecting portions extending along the same surface as the cylindrical barrel portion of the outside protecting cover, and flange-like peripheral portions integrally formed with the belt-like connecting portions so as to protrude outward.

In this case, the expanded connecting portions of the inside protecting cover and the belt-like connecting portions of the outside protecting cover do not overlap with each other when the inside protecting cover is coupled with the outside protecting cover. Furthermore, the expanded connecting portions of the inside protecting cover and the belt-like connecting portions of the outside protecting cover are alternately positioned along a same closed curve surrounding an axis of the air-fuel ratio sensing element when the inside protecting cover is coupled with the outside protecting cover. Gas holes are formed between the expanded connecting portions and the belt-like connecting portions.

It is preferable that the flange-like peripheral portion of at least one of the inside protecting cover and the outside protecting cover has an undulated surface waving along a closed curve surrounding an axis of the air-fuel ratio sensing element.

It is also preferable that the housing has a first abutting face perpendicular to an axial direction of the housing and a second abutting face extending in the axial direction of the housing. The first abutting face is brought into contact with the flange-like peripheral portions of the inside and outside protecting covers while the second abutting face supports the inner walls of cylindrical barrel portions of the inside and outside protecting covers.

According to other features of the preferred embodiments of the present invention, gas holes opened on the inside protecting cover are offset from gas holes opened on the outside protecting cover so that a gas flow path is elongated. More specifically, gas holes opened on the closed-end portions of the inside and outside protecting covers are offset from each other, so that the gas holes are not overlapped with each other when projected on a plane parallel to the closed-end portions. As a preferable arrangement, only one gas hole is opened on the closed-end portion of either the inside protecting cover or the outside protecting cover, while a plurality of gas holes are symmetrically opened on the closed-end portion of the other protecting cover.

The gas holes opened on a cylindrical wall of the inside protecting cover are offset from gas holes opened on a cylindrical wall of the outside protecting cover, so that the gas holes are not overlapped when projected on a plane parallel to the cylindrical walls. The gas holes opened on the cylindrical wall of the outside protecting cover are provided closely to the closed-end portion of the outside protecting cover. The gas holes opened on the cylindrical wall of the outside protecting cover may be arranged in a plurality of rows around an axis of the air-fuel ratio sensing element. On the contrary, the gas holes opened on the cylindrical wall of the inside protecting cover are provided closely to the open-end portion of the inside protecting cover.

Yet further, it is preferable that a trapping member for absorbing water contained in measured gas is interposed between the closed-end portions of the inside and outside protecting covers.

BRIEF DESCRIPTION OF THE DRAWINGS

The above and other objects, features and advantages of the present invention will become more apparent from the following detailed description which is to be read in conjunction with the accompanying drawings, in which:

FIG. 5 is an enlarged cross-sectional view showing a tip-end portion of the air-fuel ratio sensor shown in FIG. 1, with a dotted line showing a condition of a protruding portion of a housing before being caulked;

FIG. 6 is an enlarged cross-sectional view showing the tip-end portion of the air-fuel ratio sensor shown in FIG. 1, with arrows indicating exhaust gas flow entering through clearances;

FIG. 22 is an enlarged cross-sectional view showing a tip-end portion of an air-fuel ratio sensor in accordance with an eleventh embodiment of the present invention;

FIG. 23 is an enlarged cross-sectional view showing a tip-end portion of an air-fuel ratio sensor in accordance with a twelfth embodiment of the present invention;

DESCRIPTION OF THE PREFERRED EMBODIMENTS

Figure 1:
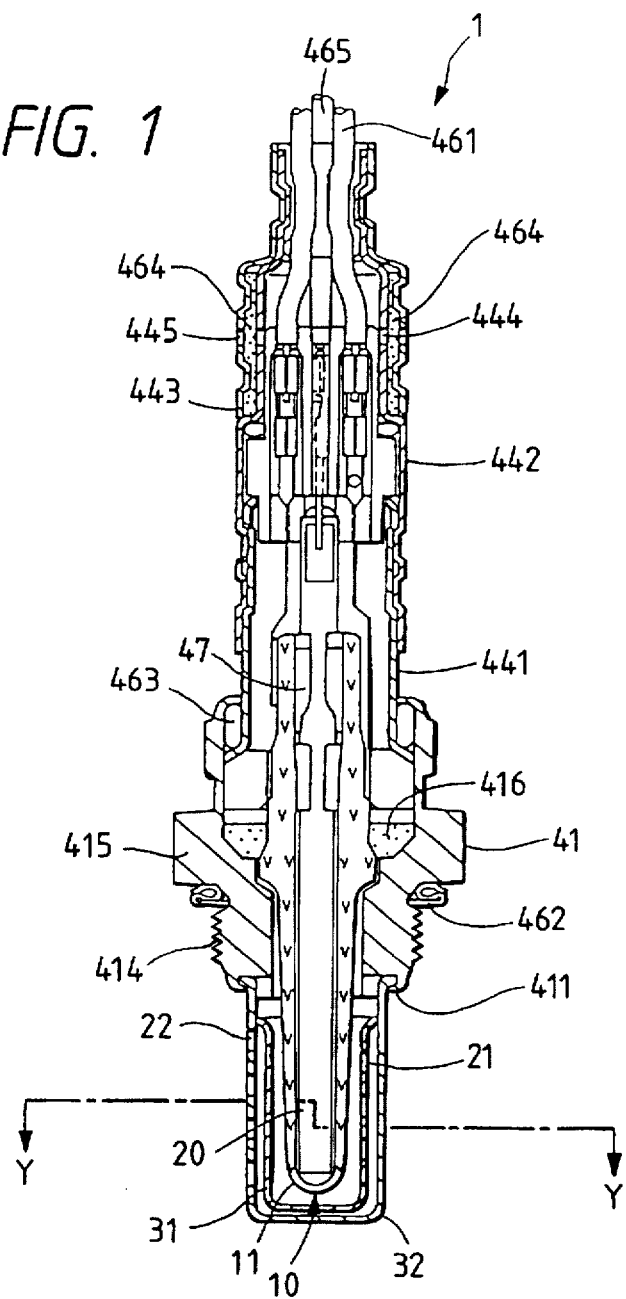
FIG. 1 is a vertical cross-sectional view showing an essential arrangement of an air-fuel ratio sensor in accordance with a first embodiment of the present invention, taken along a line X—X of FIG. 4.

Preferred embodiments of the present invention will be explained hereinafter with reference to accompanied drawings. Identical parts are denoted by the same reference numerals throughout the drawings.

First Embodiment

A first embodiment of the present invention will be explained with reference to FIGS. 1 through 6.

As shown in FIG. 1, an air-fuel ratio sensor 1 of the first embodiment comprises an oxygen concentration sensing element 10 with a cup-shaped solid electrolyte 11, a housing 41 holding this oxygen concentration sensing element 10, a stick-like heater unit 20 inserted in an inside hollow space of oxygen concentration sensing element 10, and double protecting covers 31 and 32 covering the tip-end portion of solid electrolyte 11 with gas holes 21 and 22 opened for introducing exhaust gas therethrough.

Figure 2:
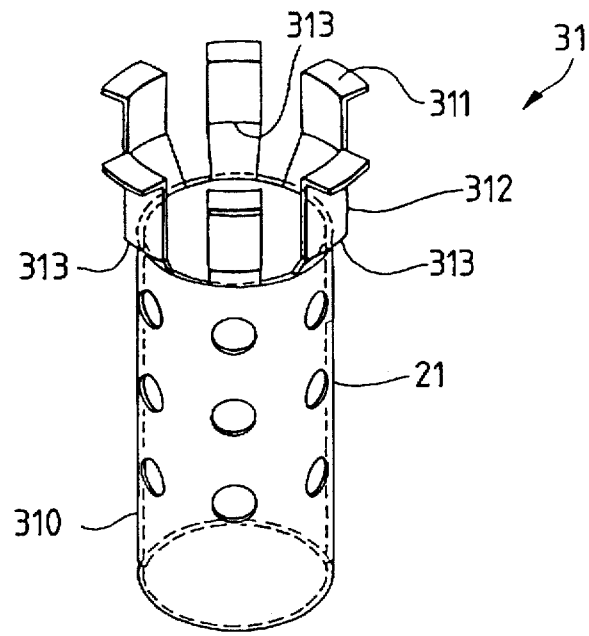
FIG. 2 is a perspective view showing an inside protecting cover used in the air-fuel ratio sensor in accordance with the first embodiment of the present invention.
Figure 3:
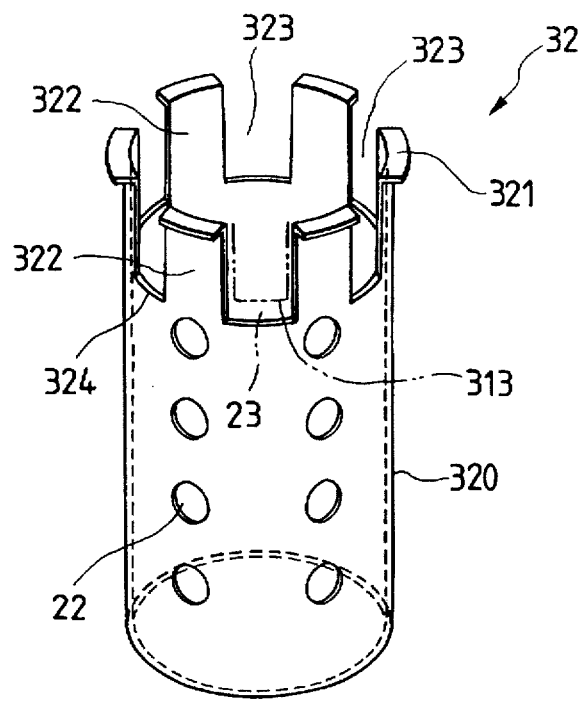
FIG. 3 is a perspective view showing an outside protecting cover used in the air-fuel ratio sensor in accordance with the first embodiment of the present invention.

The double protecting cover structure is constituted by an inside protecting cover 31 disposed closely to the solid electrolyte 11 and an outside protecting cover 32 disposed so as to surround the inside protecting cover 31. As shown in FIG. 2. inside protecting cover 31 is formed into a cup-shaped cylindrical configuration with a closed end (i.e.. bottom) and an open end (i.e., top). The circumferential open end of the cylindrical inside protecting cover 31 is split into six flange-like peripheral portions 311 which are bent radially outward. Meanwhile, as shown in FIG. 3, outside protecting cover 32 is formed into a cup-shaped cylindrical configuration with a closed end (i.e.. bottom) and an open end (i.e.. top). The circumferential open end of the cylindrical outside protecting cover 32 is split into six flange-like peripheral portions 321 which are bent radially outward. Both of inside and outside covers 31 and 32 are engageable with a protruding portion 411 provided on the housing 41 by press fitting the flange-like peripheral portions 311 and 321 inside the ridge of the protruding portion 411. Then, the protruding portion 411 is deformed or mashed radially inward by a caulking operation to securely fasten the flange-like peripheral portions 311 and 321 with the deformed part of the protruding portion 411, thereby firmly fixing the inside and outside covers 31 and 32 to the housing 41.

The flange-like peripheral portions 321 of the outside protecting cover 32 and the flange-like peripheral portions 311 of the inside protecting cover 31 are disposed alternately along the same circle (i.e., a closed curve) surrounding the oxygen concentration sensing element 10. More specifically, the radially inner edges of flange-like peripheral portions 321 of the outside protecting cover 32 are arrayed along a circle (i.e., a closed curve) having a predetermined diameter. The radially inner edges of flange-like peripheral portions 321 of the outside protecting cover 32 are arrayed along the same circle. In this case, the flange-like peripheral portions 321 and the flange-like peripheral portions 311 are not overlapped with each other.

For this arrangement, a circumferential gap between adjacent flange-like peripheral portions 321 of the outside protecting cover 32 is substantially identical with the circumferential width of a flange-like peripheral portion 311 of the inside protecting cover 31 interposed between these adjacent flange-like peripheral portions 321. In the same manner, a circumferential gap between adjacent flange-like peripheral portions 311 of the inside protecting cover 31 is substantially identical with the circumferential width of a flange-like peripheral portion 321 of the outside protecting cover 32 interposed between these adjacent flange-like peripheral portions 311.

As shown in FIG. 2, the inside protecting cover 31 comprises a cylindrical barrel portion 310 with a cylindrical wall on which a plurality of gas holes 21 are opened discretely at uniform intervals. The cylindrical barrel portion 310 has a diameter smaller than the above-described circle along which the radially inner edges of flange-like peripheral portions 311 of inside protecting cover 31 are arrayed. Each flange-like peripheral portion 311 is integrally connected to the open edge of cylindrical barrel portion 310 via a radially-expanded connecting portion 312.

As shown in FIG. 3, the outside protecting cover 32 comprises a cylindrical barrel portion 320 with a cylindrical wall on which a plurality of gas holes 22 are opened discretely at uniform intervals. The cylindrical barrel portion 320 has a diameter substantially identical with the above-described circle along which the radially inner edges of flange-like peripheral portions 321 of outside protecting cover 32 are arrayed. Each flange-like peripheral portion 321 is integrally connected to the cylindrical portion 320 via a belt-like connecting portion 322 extending along the same surface as the cylindrical wall of cylindrical barrel portion 320.

The radially-expanded connecting portion 312 and the belt-like connecting portion 322 are not overlapped with each other and are alternately arranged along the closed curve surrounding the oxygen concentration sensing element 10. Namely, when radially-expanded connecting portion 312 and belt-like connecting portion 322 are coupled, they cooperatively constitute a cylindrical cover body with clearances 23 (FIG. 3) formed between them. Exhaust gas is introduced inside the protecting covers 31 and 32 through the clearance 23.

The upper-end surfaces (i.e., distal end surfaces) of radially-expanded connecting portions 312 of the inside protecting cover 31 are disposed along the same closed curve along which the belt-like connecting portions 322 are disposed. Thus, when the inside protecting cover 31 is assembled with the outside protecting cover 32, the radially-expanded connecting portions 312 matches with a corresponding cutout 323 formed between adjacent connecting portions 322 of the outside protecting cover 32.

The lower-end portion (i.e. a base-end portion) of radially-expanded connecting portion 312 is bent inward along a horizontal folding line 313 (refer to FIG. 2). The folding line 313 is positioned at a level offset upward from a lower edge line 324 of the cutout 323, when the inside and outside protecting covers 31 and 32 are installed on the housing 41. Thus, the clearance 23 is formed between the lower edge line 324 and the folding line 313 as shown in FIG. 3.

Figure 4:
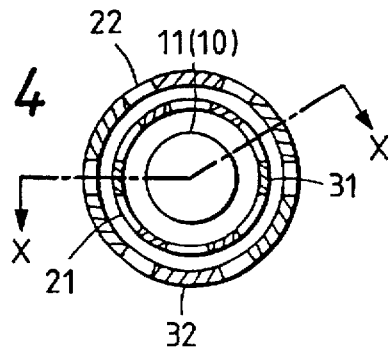
FIG. 4 is a horizontal cross-sectional view showing the air-fuel ratio sensor in accordance with the first embodiment of the present invention, taken along a line Y—Y of FIG. 1.

Furthermore, as shown in FIGS. 2 through 4, gas holes 21 and 22 are disposed alternately, so that gas holes 21 do not confront directly with gas holes 22. The housing 41, as shown in FIG. 5, has a ring groove comprising a first abutting face 412 perpendicular to the axial direction of the housing 41 and a second abutting face 413 extending along the axial direction from the inner edge of the first face 412.

The upper horizontal surfaces of flange-like peripheral portions 311 and 321 of the inside and outside protecting covers 31 and 32 are directly brought into contact with the first abutting face 412 of housing 41 when the inside and outside protecting covers 31 and 32 are fixed to the housing 41 by a caulking operation. The upper inside surfaces of the cylindrical walls of the inside and outside protecting covers 31 and 32 are directly brought into contact with the second abutting face 413.

The air-fuel ratio sensor 1 of the first embodiment is used to detect an air-fuel ratio of an internal combustion engine for an automotive vehicle. As shown in FIG. 1, the housing 41 comprises a screw portion 414 engaged with a screw hole opened at an appropriate portion of an exhaust gas passage, and a flange portion 415 secured to the wall of an exhaust gas pipe. The protruding portion 411 is provided at the lower edge (i.e., a portion opposed to the flange portion 415) of the housing 41. The protruding portion 411, as indicated by a dotted line in FIG. 5, extends straight along the axial direction of the housing 41. In installation, the flange-like peripheral portions 311 and 321 of the inside and outside protecting covers 31 and 32 are fixed by deforming the protruding portion 411 radially inward.

Furthermore, as shown in FIG. 1, atmospheric covers 441, 442 and 443 are sequentially provided at the base end side of air-fuel ratio sensor 1. A plurality of air holes 444 and 445 are provided on the walls of atmospheric covers 442 and 443 to introduce fresh air into an inside chamber of oxygen concentration sensing element 10.

The oxygen concentration sensing element 10 is securely held by the housing 41 with talc 416 interposed between them. In FIG. 1, reference numeral 462 denotes a gasket, reference numeral 463 denotes a metallic ring, and reference numeral 464 denotes a gas-permeable and waterproof filter.

The heater unit 20 is inserted inside the oxygen concentration sensing element 10. The heater unit 20 is supported to the oxygen concentration sensing element 10 by a holder 47. The heater unit 20 comprises a heater element (not shown) which is connected to a power supply lead 465. Signal lines 461 are connected to electrodes (not shown) provided on the inside and outside wall surfaces of the electrolyte 11 of the oxygen concentration sensing element 10.

Signal lines 461 and power supply line 465 are supported to the atmospheric covers 442 and 443 through a bush. Flesh air introduced from the air holes 444 and 445 is guided via an air passage (not shown) to the inside chamber (not shown) of the oxygen concentration sensing element 10.

Next, functions and effects of the air-fuel ratio sensor 1 of the first embodiment will be explained.

The inside and outside protecting covers 31 and 32 are fixed to the housing 41 by a caulking operation because the caulking operation is easy to control or administrate the manufacturing conditions compared with a welding operation.

Inside and outside protecting covers 31 and 32 are provided with flange-like peripheral portions 311 and 321 at their open-end portions. Flange-like peripheral portions 311 and 321 protrude radially outward. These flange-like peripheral portions 311 and 321 are placed on the first abutting face 412 and fixed firmly and tightly by mashing or deforming the protruding portion 411 on the upper surfaces of flange-like peripheral portions 311 and 321. Accordingly, no air gap is formed between the flange-like peripheral portions 311 and 321 and the protruding portion 411. Accordingly, there is no necessity of inserting an intervening member, such as a ring, between them.

Furthermore, the flange-like peripheral portions 311 and 321 of inside and outside protecting covers 31 and 32 are disposed alternately along a closed curve surrounding the outer wall of the oxygen concentration sensing element 10, so that the flange-like peripheral portions 311 and 321 are not overlapped with each other in the direction of this closed curve. In other words, in a caulking operation, any part of the protruding portion 411 presses either the flange-like peripheral portion 311 of inside protecting cover 31 or the flange-like peripheral portion 321 of outside protecting cover 32, not both of them.

This arrangement is advantageous in that the machining operation for fabricating the flange-like peripheral portions 311 and 321 can be simplified greatly, because the configuration of the flange-like peripheral portions 311 of inside protecting cover 31 needs not to match accurately with the configuration of the flange-like peripheral portions 321 of outside protecting cover 32.

Furthermore, this arrangement is advantageous in that a pressing force required for the caulking operation can be reduced because of elimination of the overlap between the flange-like peripheral portions. Thus, the caulking operation can be performed easily.

Furthermore, the alternate arrangement of the flange-like peripheral portions 311 and 321 of inside and outside protecting covers 31 and 32 establishes a constant positional relationship between the inside protecting cover 31 and the outside protecting cover 32 around their axes. Hence, it becomes possible to determine a univocal relationship between gas holes 21 opened on the wall of inside protecting cover 31 and gas holes 31 opened on the wall of outside protecting cover 32 about their axes once a positional relationship between the gas holes 21 and 22 and the flange-like peripheral portions 311 and 321 is determined adequately.

When both of the protecting covers 31 and 32 are installed on the housing 41, clearances 23 are formed between these protecting covers 31 and 32 due to the structural difference between radially-expanded connecting portion 312 and the belt-like connecting portions 322, as shown in FIG. 3.

More specifically, as indicated by arrows in FIG. 6, exhaust gas is introduced through these clearances 23. In other words, each clearance 23 acts as a sort of gas hole. It means that the number of gas holes 21 and 22 opened on the walls of protecting covers 31 and 32 can be reduced. And, the exhaust gas can be introduced uniformly from all directions.

Furthermore, as shown in FIG. 5, the housing 41 is formed with the ring groove comprising first abutting face 412 perpendicular to the axial direction of housing 41 and second abutting face 413 extending along the axial direction from the inner edge of the first face 412. The second abutting face 413 is directly brought into contact with the inside surfaces of the cylindrical walls of the inside and outside protecting covers 31 and 32. Thus, the inside and outside protecting covers 31 and 32 can be firmly supported from inside by the second abutting face 413 of housing 41. Hence, the inside and outside protecting covers 31 and 32 can be firmly fixed to the housing 41.

It is be possible to determine the sizes of protecting covers 31 and 32 so that the protecting covers 31 and 32 are press fitted along the second abutting face 413. Alternatively, it is possible to determine the sizes of protecting covers 31 and 32 so that the protecting covers 31 and 32 are loosely coupled with the second abutting face 413. In this case, the protecting covers 31 and 32 are fixedly sandwiched between the protruding portion 411 and the second abutting face 413 by mashing or deforming the protruding portion 411 by a caulking operation.

As described above, the first embodiment of the present invention provides an air-fuel ratio sensor 1 having an excellent inside and outside protecting covers 31 and 32 simple in construction, excellent in rigidity, and easy to install.

According to the first embodiment, the protecting covers are fixed to the housing by a caulking operation. Thus, there is no necessity of using a welding operation. In other words, the problems relating to the welding operation described previously in the description of the related art can be eliminated.

Furthermore, the portions to be fixed to the housing by the caulking operation are flange-like peripheral portions which are bent outward so as to be tightly brought into contact with the abutting surface of the housing. This arrangement is advantageous in that any intervening member, such as a ring, is no longer required to fill the vacant space. Thus, the number of parts is increased.

Furthermore, the flange-like peripheral portions of the inside protecting cover and the flange-like peripheral portions of the outside protecting cover are disposed alternately along a closed curve surrounding the outer wall of the air-fuel ratio sensing element, so that the flange-like peripheral portions of the inside protecting cover are not overlapped with the flange-like peripheral portions of the outside protecting cover. In other words, there is no necessity of increasing the pressing force in a caulking operation for fixing the overlapped bent portions of the protecting covers to the housing.

More specifically, the first embodiment of the present invention provides an air-fuel ratio sensor comprising an air-fuel ratio sensing element with a solid electrolyte having a detecting portion for detecting a gas concentration of measured gas, a housing for holding the air-fuel ratio sensing element, and protecting means for covering the detecting portion of the solid electrolyte, the protecting means having gas holes opened for introducing measured gas. The protecting means of the first embodiment comprises an inside protecting cover disposed closely to the solid electrolyte and an outside protecting cover surrounding this inside protecting cover. The inside protecting cover is formed into a cup-shaped cylindrical configuration having a closed-end portion at one end and an opened-end portion at the other end. At least one flange-like peripheral portion protruding outward is formed at the opened-end portion of the inside protecting cover. The outside protecting cover is formed into a cup-shaped cylindrical configuration having a closed-end portion at one end and an opened-end portion at the other end. At least one flange-like peripheral portion protruding outward is formed at the opened-end portion of said outside protecting cover. And, the flange-like peripheral portion of the inside protecting cover and the flange-like peripheral portion of the outside protecting cover are fixed to the housing by a caulking operation.

Second Embodiment

Figure 7:
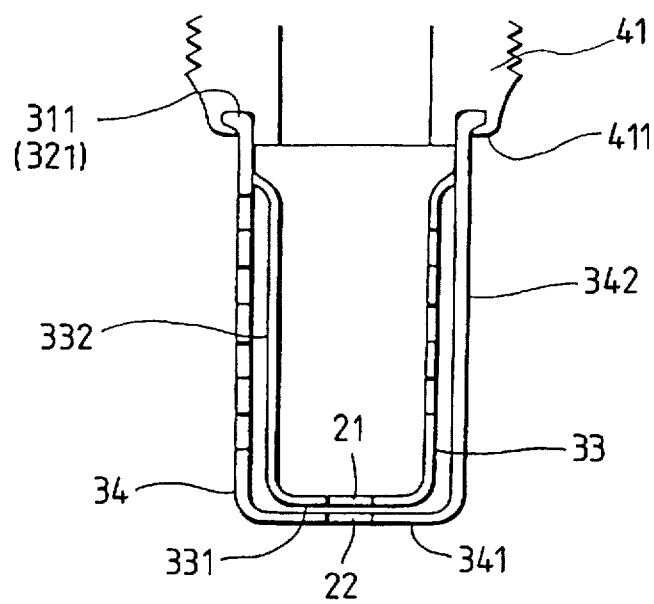
FIG. 7 is a vertical cross-sectional view showing the housing and the protecting covers in accordance with a second embodiment of the present invention.

A second embodiment of the present invention, as shown in FIG. 7, provides an air-fuel ratio sensor having an inside protecting cover 33 having a bottom 331 with a gas hole 21 and an outside protecting cover 34 having a bottom 341 with a gas hole 22.

Providing gas holes 21 and 22 on the bottom surfaces 331 and 341 is advantageous in that the number of gas holes 21 on side walls 332 and 342 of protecting covers 33 and 34 can be reduced, and in that the exhaust gas can be introduced in the protecting covers 33 and 34 from the direction of the bottoms 331 and 341 (i.e., an axial direction) in addition to the radial directions of side walls 332 and 342 (i.e., angular directions).

Furthermore, gas holes 21 and 22 formed on the bottom surfaces 331 and 341 serve as drain holes for draining water condensed from the exhaust gas and settling on the bottom surfaces 331 and 341 of the protecting covers 33 and 34.

Other arrangements are substantially the same as those disclosed in the first embodiment.

Third Embodiment

Figure 8:
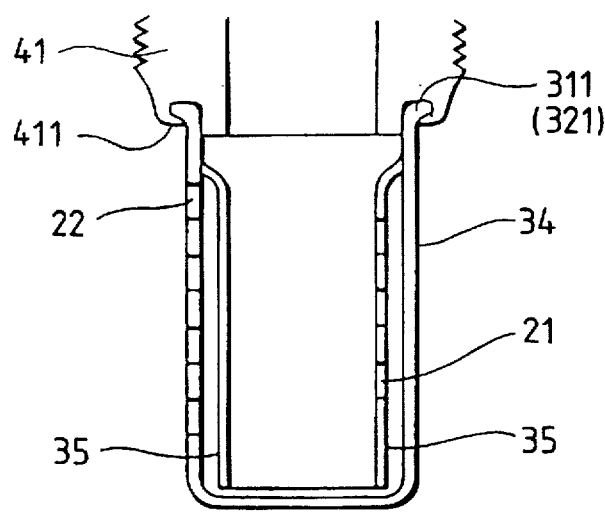
FIG. 8 is a vertical cross-sectional view showing the housing and the protecting covers in accordance with a third embodiment of the present invention.

A third embodiment of the present invention, as shown in FIG. 8, provides an air-fuel ratio sensor having an inside protecting cover 35 with an opened bottom. According to the arrangement of the third embodiment, the inside protecting cover 35 can be simplified in structure. There is no necessity of opening gas hole 21 on the bottom of the inside protecting cover 35.

Other arrangements are substantially the same as those disclosed in the first embodiment.

Fourth Embodiment

Figure 9:
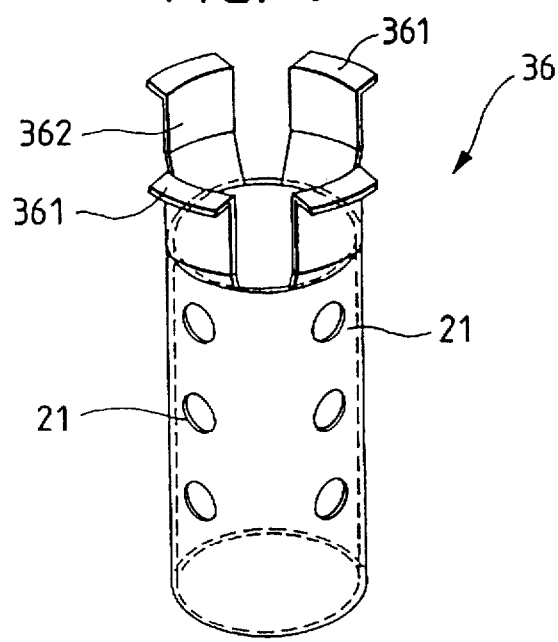
FIG. 9 is a perspective view showing an inside protecting cover in accordance with a fourth embodiment of the present invention.
Figure 10:
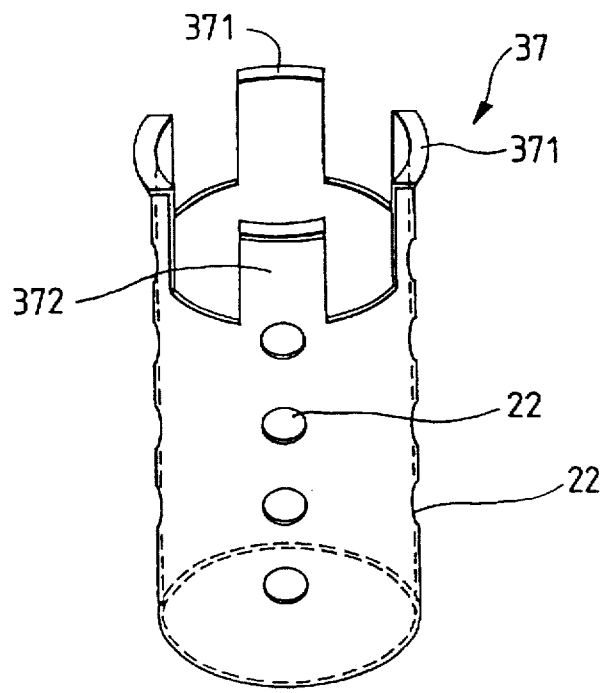
FIG. 10 is a perspective view showing an outside protecting cover in accordance with the fourth embodiment of the present invention.

A fourth embodiment of the present invention, as shown in FIGS. 9 and 10, provides an air-fuel ratio sensor differentiated by the numbers of the flange-like peripheral portions and the connecting portions.

More specifically, a total of four flange-like peripheral portions 361 are provided at an open-end side of the inside protecting cover 36. Each flange-like peripheral portion 361 protrudes radially outward and is connected to the cylindrical wall of inside protecting cover 36 via a radially-expanded portion 362.

Similarly, a total of four flange-like peripheral portions 371 are provided at an open-end side of the outside protecting cover 37. Each flange-like peripheral portion 371 protrudes radially outward and is connected to the cylindrical wall of outside protecting cover 37 via a belt-like connecting portion 372.

Except for the number of the flange-like peripheral portions and the connecting portions, arrangements are substantially identical with those disclosed in the first embodiment.

Fifth Embodiment

Figure 11:
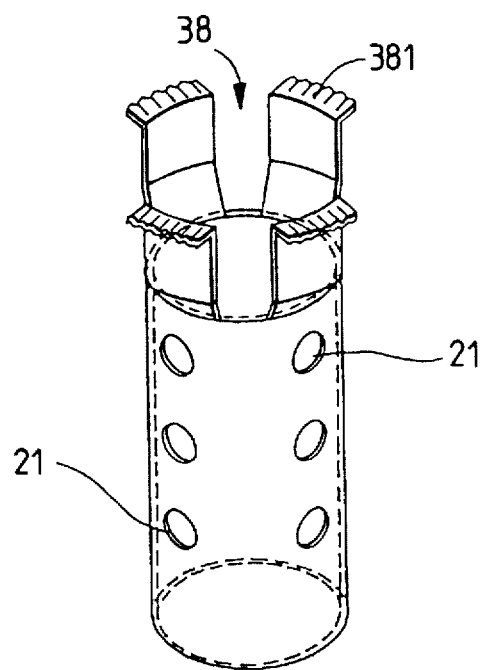
FIG. 11 is a perspective view showing an inside protecting cover in accordance with a fifth embodiment of the present invention.
Figure 12:
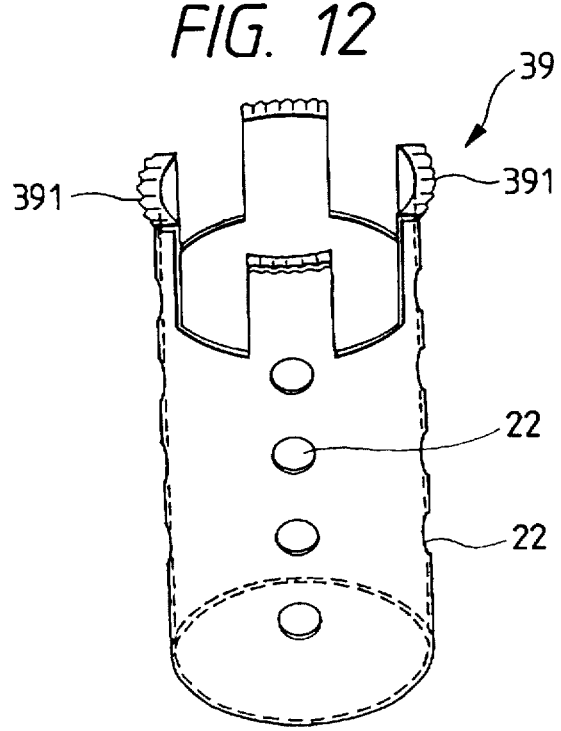
FIG. 12 is a perspective view showing an outside protecting cover in accordance with the fifth embodiment of the present invention.

A fifth embodiment of the present invention, as shown in FIGS. 11 and 12, provides an air-fuel ratio sensor having flange-like peripheral portions 381 and 391 whose surfaces are undulated.

Each of flange-like peripheral portions 381 and 391 has an undulated surface waving in an up-and-down direction along a closed curve surrounding the outer wall of oxygen concentration sensing element 10, rather than being finished to a flush surface.

This arrangement is advantageous in that, when the protecting covers are press fitted to the protruding portion 411 of housing 41, the waved portion bites firmly into the protruding portion 411. Thus, the caulking portion can be enhanced and stabilized. Other arrangements are substantially the same as those disclosed in the fourth embodiment.

In the above-described embodiments, it is possible to eliminate either gas holes 21 or gas holes 22 or both of them, as far as the clearances 23 are formed between the inside and outside protecting covers.

Sixth Embodiment

A sixth embodiment of the present invention provides an air-fuel ratio sensor having an inside protecting cover and an outside protecting cover whose gas holes are offset from each other.

Figure 13:
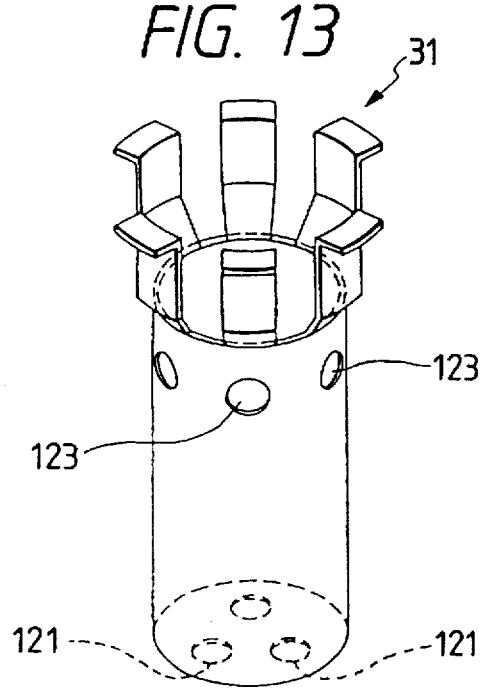
FIG. 13 is a perspective view showing an inside protecting cover in accordance with a sixth embodiment of the present invention.

As shown in FIGS. 13 ad 14, gas holes 121 are opened on a bottom (i.e., closed end) of the inside protecting cover 31, and a gas hole 122 is opened on a bottom (i.e. closed end) of the outside protecting cover 32. The bottom surface of inside protecting cover 31 is substantially parallel to the bottom surface of outside protecting cover 32. The gas holes 121 opened on the inside protecting cover 31 are offset from the gas hole 122 opened on the outside protecting cover 32. This radial offset arrangement is advantageous to elongate the gas flow path along which measure gas reaches the electrolyte 11 of the oxygen concentration sensing element 10 from the direction of the bottoms of protecting covers 31 and 32.

A total of three gas holes 121, opened on the bottom of inside protecting cover 31, are spaced radially from an axis C (FIG. 5) of oxygen concentration sensing element 10 and are positioned symmetrically about this axis C. On the other hand, only one gas hole 122, opened on the bottom of outside protecting cover 32, is position on the axis C.

A total of six gas holes 123 are opened on the cylindrical wall of the inside protecting cover 31. A total of six gas holes 124 are opened on the cylindrical wall of the outside protecting cover 32. Gas holes 123 opened on the inside protecting cover 31 are offset in the axial direction from gas holes 124 opened on the outside protecting cover 32. More specifically, gas holes 123 are positioned at the opened-end side of the inside protecting cover 31, while gas holes 124 are positioned at the closed-end side of the outside protecting cover 32. This axial offset arrangement is advantageous to elongate the gas flow path along which measure gas reaches the electrolyte 11 of the oxygen concentration sensing element 10 from the directions of the side walls of the protecting covers 31 and 32.

Figure 26:
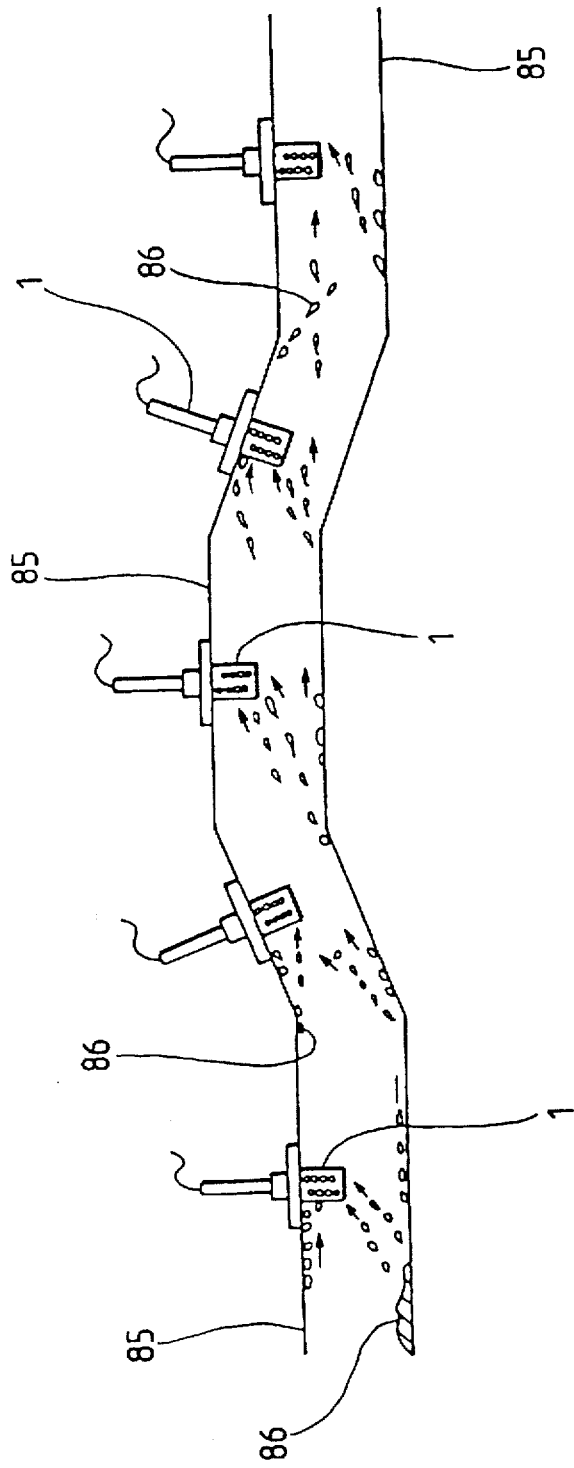
FIG. 26 is a view showing an exhaust gas pipe and air-fuel ratio sensors installed on this exhaust gas pipe, with a behavior of condensed water.
Figure 27:
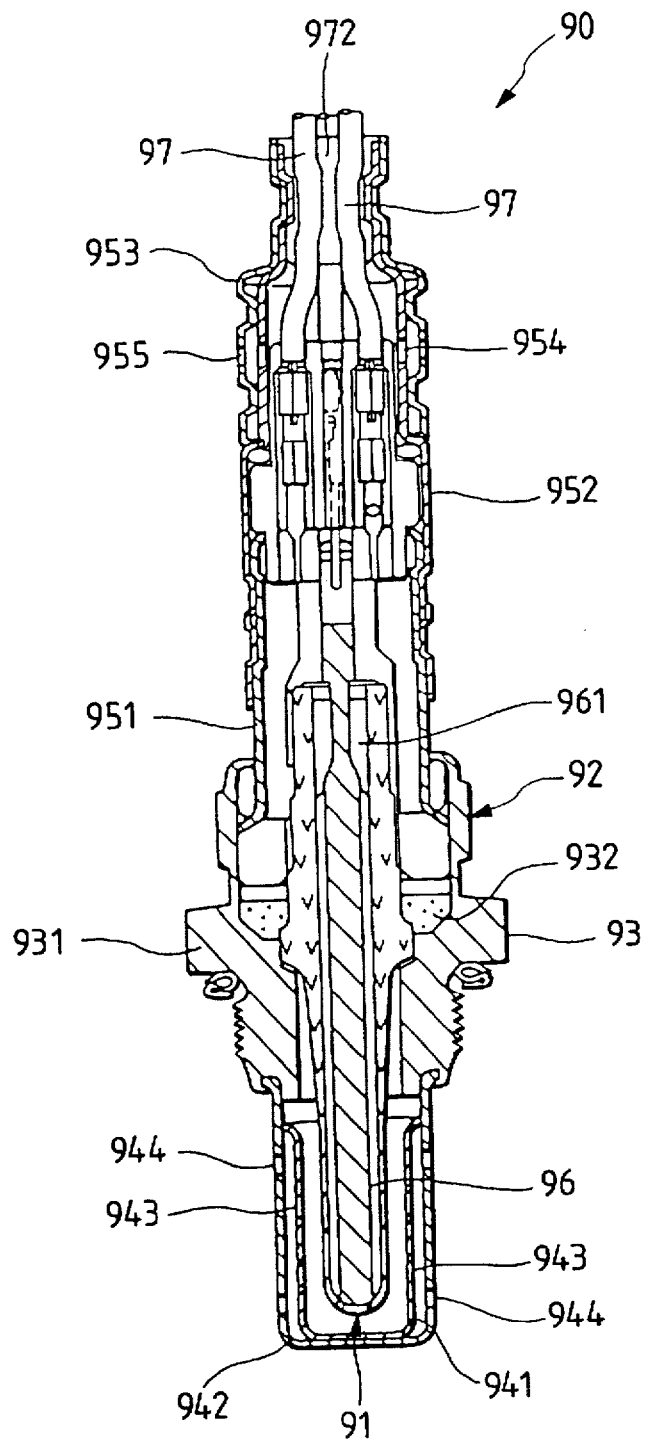
FIG. 27 is a vertical cross-sectional view showing an essential arrangement of a conventional air-fuel ratio sensor.

As shown in FIG. 26, air-fuel ratio sensors 1 are mainly disposed on the exhaust gas pipe 85 provided downstream of an exhaust gas manifold of an internal combustion engine, rather than provided directly on the exhaust gas manifold. This arrangement is effective to prevent air-fuel ratio sensors 1 from being exposed to high-temperature exhaust gas or to detect an oxygen concentration in the exhaust gas downstream of a catalytic converter.

When the air-fuel ratio sensor 1 is installed on the wall of exhaust gas pipe 85, the gas holes 124 opened on the outside protecting cover 32 are positioned closely to the center of the exhaust gas pipe 85 where the flow speed of the exhaust gas is relatively large.

The gas holes 123 opened on the inside protecting cover 31 are positioned far from the heater unit 20 inserted in the solid electrolyte 11 to quickly warm up the oxygen concentration sensing element 10. In other words, gas holes 123 are positioned closely to the base-end portion of the oxygen concentration sensing element 10 where the temperature is relatively low.

Other arrangements are substantially the same as those disclosed in the first embodiment.

Figure 14:
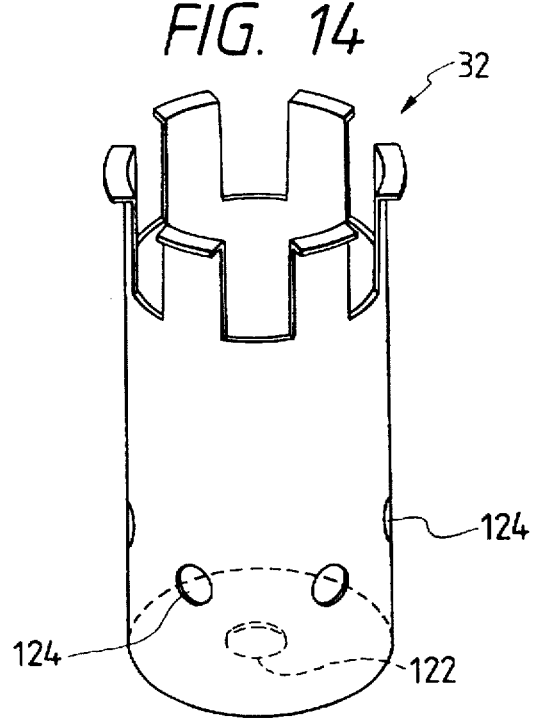
FIG. 14 is a perspective view showing an outside protecting cover in accordance with the sixth embodiment of the present invention.

Next, functions and effects of the sixth embodiment will be explained. As shown in FIGS. 13 and 14, according to the air-fuel ratio sensor 1 of the sixth embodiment, the gas holes 121 opened on the bottom of inside protecting cover 31 are offset from the gas hole 122 opened on the bottom of outside protecting cover 32. Thus, the gas flow path can be desirably elongated. The elongation of the gas flow path is effective to suppress water condensed in the exhaust gas pipe from reaching the oxygen concentration sensing element 10.

More specifically, as shown in FIG. 26, most of condensed water 86 settles on the bottom of the exhaust gas pipe 85. Upon start-up of the engine, the condensed water 86 is blown upward by the exhaust gas emitted from the engine. Accordingly, after reaching the inside and outside protecting covers 31 and 32, the condensed water 86 enters from the bottoms of inside and outside protecting covers 31 and 32 and then advances upward.

However, according to the sixth embodiment of the present invention, the gas holes 121 opened on the bottom of inside protecting cover 31 are offset from the gas hole 122 opened on the bottom of outside protecting cover 32. Accordingly, the upward advance of the condensed water 86 is interrupted by this offset arrangement. Thus, it becomes possible to effectively suppress the condensed water 86 from reaching the oxygen concentration sensing element 10.

Furthermore, according to the sixth embodiment of the present invention, gas holes 123 and 124 are provided on the cylindrical walls of the inside and outside protecting covers 31 and 32. These gas holes 123 and 124 are offset from each other so as to extend the gas flow path along which the exhaust gas reaches the solid electrolyte 11 of oxygen concentration sensing element 10. Accordingly, it becomes difficult for the condensed water 86 contained in the exhaust to easily reach the solid electrolyte 11 of oxygen concentration sensing element 10. The cylindrical walls of the inside and outside protecting covers 31 and 32, on which gas holes 123 and 124 are provided, face directly to the flow of the exhaust gas. Hence, the exhaust gas can be introduced effectively and quickly from the gas holes 123 and 124. This is advantageous to improve the response of the air-fuel ratio sensor 1.

Still further, the gas holes 124 opened on the cylindrical wall of the outside protecting cover 32 are positioned closely to the center of the exhaust gas pipe 85 when the air-fuel ratio sensor 1 is installed on the wall of the exhaust gas pipe 85. The center of the exhaust gas pipe 85 is a portion where the speed of the exhaust gas flowing in the exhaust gas pipe 85 becomes maximum. Hence, it becomes possible to effectively introduce the exhaust gas from these gas holes 124.

On the other hand, the gas holes 123 opened on the cylindrical wall of the inside protecting cover 31 are positioned closely to the base-end portion of the oxygen concentration sensing element 10 where the temperature is relatively low. This is effective to prevent the oxygen concentration sensing element 10 from being cracked due to invasion of condensed water 86. More specifically, cracks tend to occur in a high-temperature region of the oxygen concentration sensing element 10. To prevent such cracks, it is desirable to guide the condensed water 86 to the lower-temperature region in the event the condensed water 86 is entered accidentally. In this respect, the arrangement of the sixth embodiment is desirable since the condensed water 86 is surely guided toward the lower-temperature region by the gas holes 123 opened on the inside protecting cover 31. Thus, a thermal stress caused by invasion of condensed water 86 can be suppressed to a smaller value, suppressing the generation of cracks.

Yet further, as shown in FIG. 13, gas holes 121 opened on the bottom of inside protecting cover 31 are spaced from the axis C of the oxygen concentration sensing element 10 and symmetrically arranged. Meanwhile, as shown in FIG. 14, the gas hole 122 opened on the bottom of outside protecting cover 32 is positioned just on this axis C. This arrangement is effective to prevent the condensed water 86 from entering inside the protecting covers 31 and 32 because the gas holes 121 of inside protecting cover 31 can be offset from the gas hole of outside protecting cover 32. Thus, the amount of a thermal stress caused by the invasion of condensed water 86 can be reduced significantly, reducing the probability of causing cracks.

According to the experiments conducted by the inventors, no condensed water was found in an air-fuel ratio sensor having an arrangement of the sixth embodiment of the present invention, while the condensed water was found at a percentage of 80% in a conventional air-fuel ratio sensor.

In short, the sixth embodiment of the present invention provides an air-fuel ratio sensor having gas holes opened on an inside protecting cover and gas holes opened on an outside protecting cover which are offset from each other so that a gas flow path can be elongated. More specifically, the gas holes opened on a closed-end portion of the inside protecting cover are offset from gas holes opened on a closed-end portion of the outside protecting cover, so that the gas holes are not overlapped when projected on a plane substantially parallel to these closed-end portions. Furthermore, gas holes opened on a cylindrical wall of the inside protecting cover are offset from gas holes opened on a cylindrical wall of the outside protecting cover, so that the gas holes are not overlapped with each other when projected on a plane substantially parallel to the cylindrical walls.

It is preferable that the gas holes opened on the bottom of the inside protecting cover are spaced from the center of the oxygen concentration sensing element. With this arrangement, it becomes possible to keep a relatively large distance between the oxygen concentration sensing element and the condensed water once it enters through the gas holes of the inside protecting cover.

Seventh Embodiment

Figure 15:
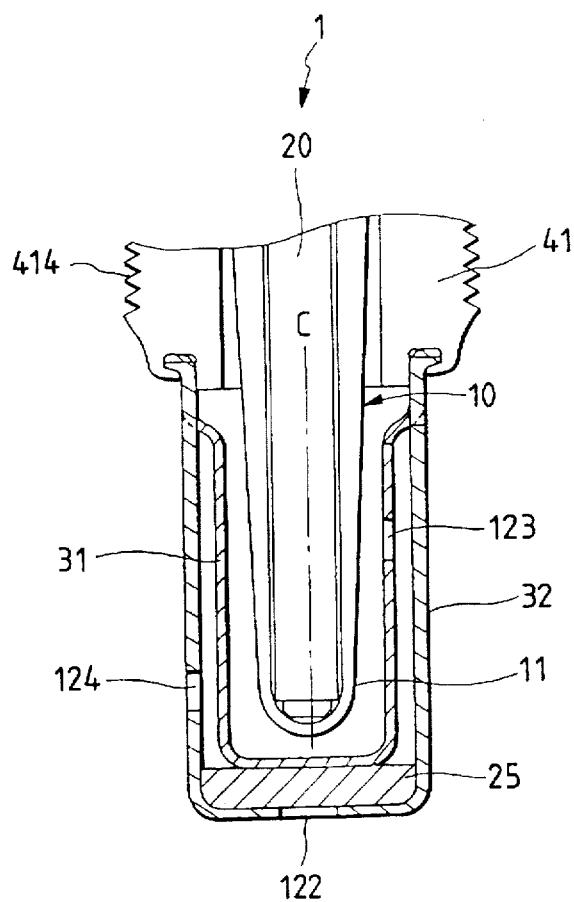
FIG. 15 is an enlarged cross-sectional view showing a tip-end portion of an air-fuel ratio sensor in accordance with a seventh embodiment of the present invention.

A seventh embodiment of the present invention, as shown in FIG. 15, provides an air-fuel ratio sensor having a trapping member 25 for absorbing the condensed water 86 once it enters into the air-fuel ratio sensor 1.

More specifically, a trapping member 25 is interposed between the bottom surface of inside protecting cover 31 and the bottom surface of outside protecting cover 32.

The trapping member 25 is made of ceramic crystalline fiber, sintered porous sheet, or metallic mesh sheet. With the provision of trapping member 25, it becomes possible to interrupt the condensed water 86 from reaching the oxygen concentration sensing element 10. Other arrangements are substantially the same as those disclosed in the first embodiment.

Eighth Embodiment

Figure 16:
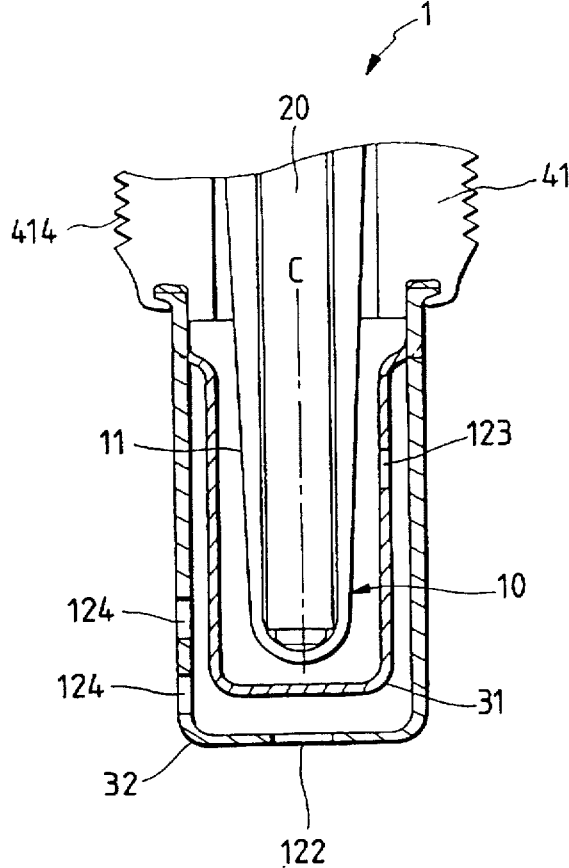
FIG. 16 is an enlarged cross-sectional view showing a tip-end portion of an air-fuel ratio sensor in accordance with an eighth embodiment of the present invention.
Figure 17:
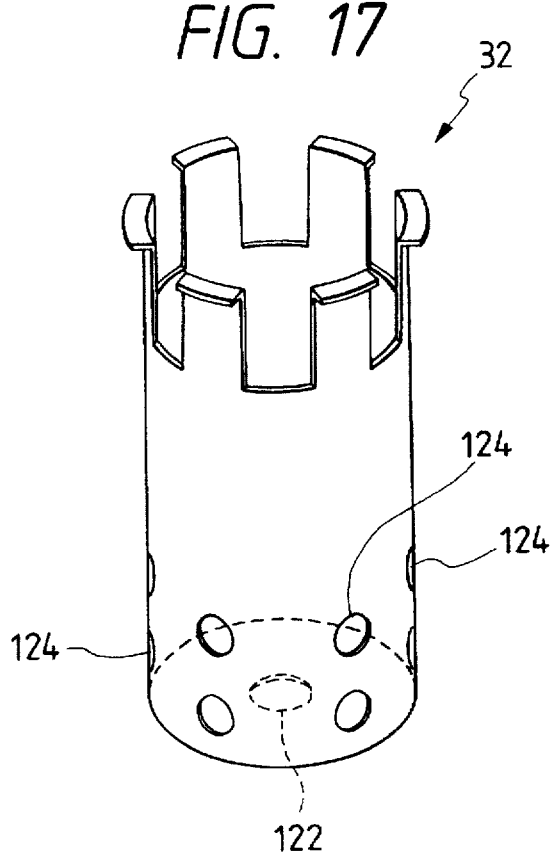

An eighth embodiment of the present invention, as shown in FIGS. 16 and 17, provides an air-fuel ratio sensor having outside protecting cover 32 with gas holes 124 arranged in two rows around the axis C of the oxygen concentration sensing element 10. Other arrangements are substantially the same as those disclosed in the first embodiment.

Ninth Embodiment

Figure 18:
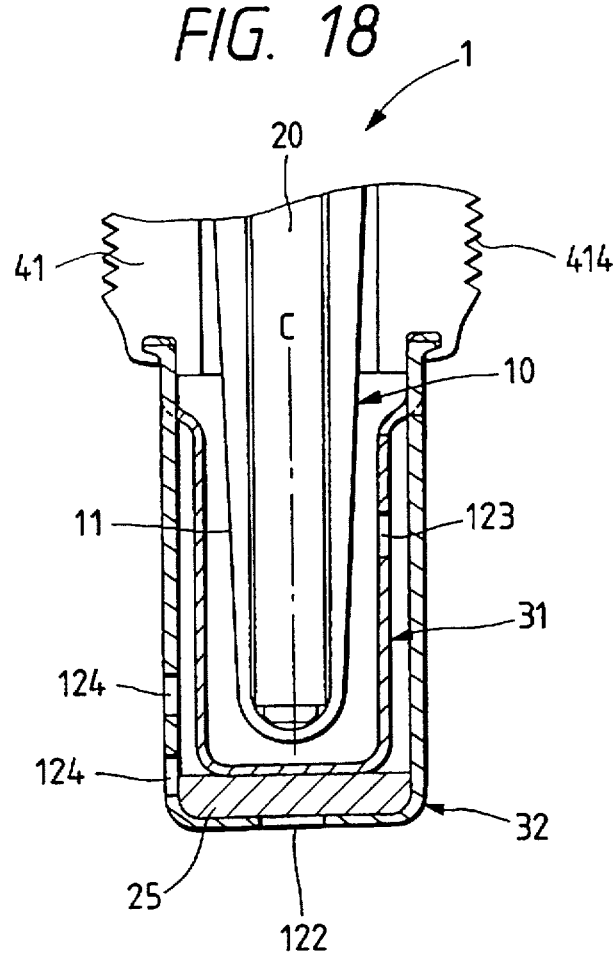
FIG. 18 is an enlarged cross-sectional view showing a tip-end portion of an air-fuel ratio sensor in accordance with a ninth embodiment of the present invention.

A ninth embodiment of the present invention, as shown in FIG. 18, provides an air-fuel ratio sensor similar to the eighth embodiment but different in that trapping member 25 is interposed between the bottom of the inside protecting cover 31 and the outside protecting cover 32.

Tenth Embodiment

Figure 19:
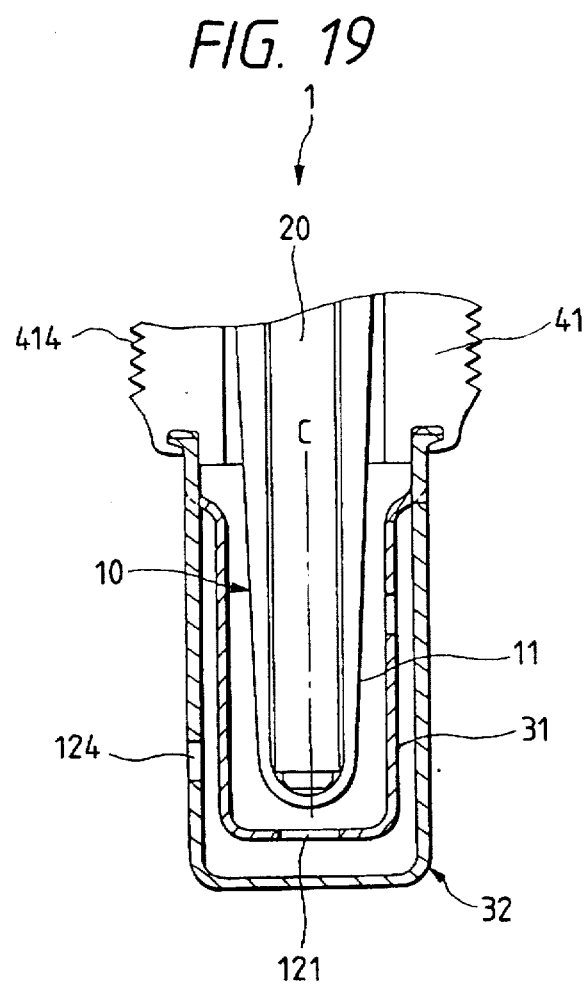
FIG. 19 is an enlarged cross-sectional view showing a tip-end portion of an air-fuel ratio sensor in accordance with a tenth embodiment of the present invention.
Figure 20:
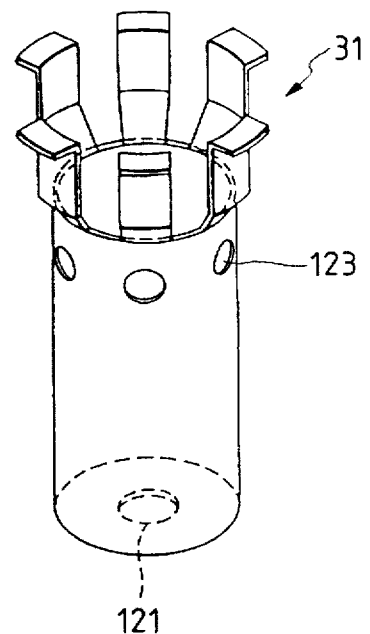
FIG. 20 is a perspective view showing an inside protecting cover in accordance with the tenth embodiment of the present invention.
Figure 21:
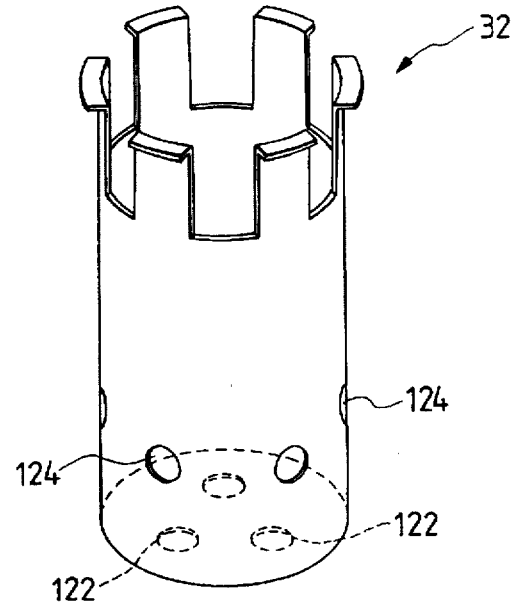
FIG. 21 is a perspective view showing an outside protecting cover in accordance with the tenth embodiment of the present invention.

A tenth embodiment of the present invention, as shown in FIGS. 19 to 21, provides an air-fuel ratio sensor similar to the sixth embodiment but different in that the layout of gas holes provided on the bottoms of inside protecting cover 31 and outside protecting cover 32 is reversed.

More specifically, only one gas hole 121 is provided on the bottom of inside protecting cover 31 while three gas holes 122 are provided on the bottom of outside protecting cover 32. Gas hole 121 is positioned on the axis C of the oxygen concentration sensing element 10. Gas holes 122 are spaced from the axis C and disposed symmetrically about this axis C.

Eleventh Embodiment

An eleventh embodiment of the present invention, as shown in FIG. 22, provides an air-fuel ratio sensor similar to the tenth embodiment but different in that trapping member 25 is interposed between the bottom of the inside protecting cover 31 and the outside protecting cover 32.

Twelfth Embodiment

Figure 24:
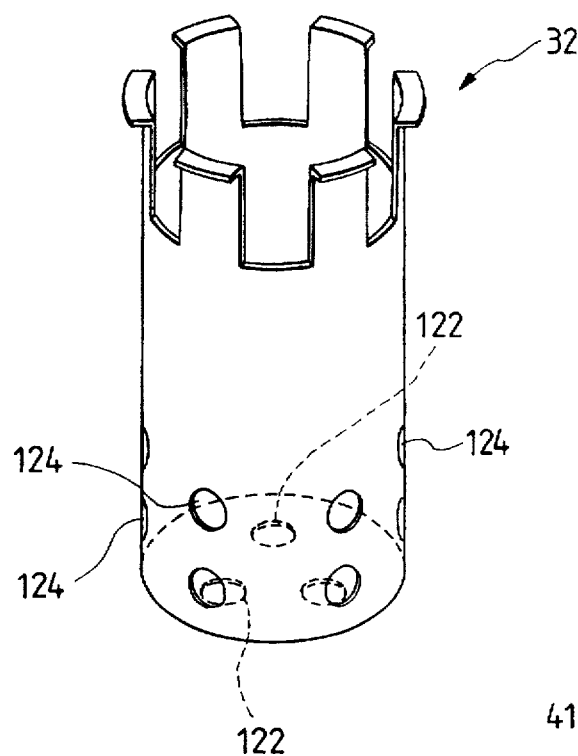
FIG. 24 is a perspective view showing an outside protecting cover in accordance with the twelfth embodiment of the present invention.

A twelfth embodiment of the present invention, as shown in FIGS. 23 and 24, provides an air-fuel ratio sensor similar to the eighth embodiment but different in that the layout of gas holes provided on the bottoms of inside protecting cover 31 and outside protecting cover 32 is reversed.

More specifically, only one gas hole 121 is provided on the bottom of inside protecting cover 31 while three gas holes 122 are provided on the bottom of outside protecting cover 32. Gas hole 121 is positioned on the axis C of the oxygen concentration sensing element 10. Gas holes 122 are spaced from the axis C and disposed symmetrically about this axis C.

Thirteenth Embodiment

Figure 25:
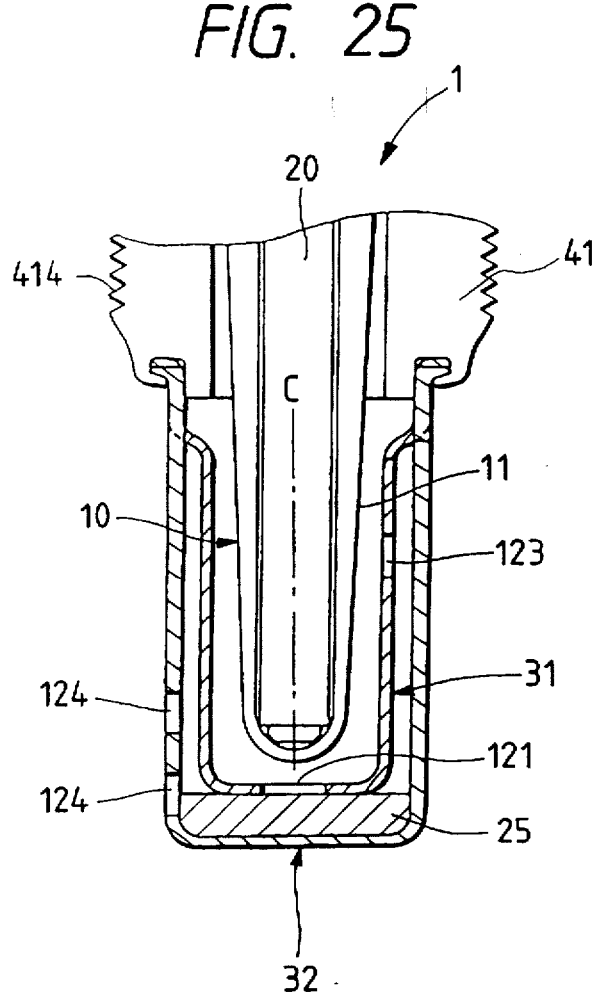
FIG. 25 is an enlarged cross-sectional view showing a tip-end portion of an air-fuel ratio sensor in accordance with a thirteenth embodiment of the present invention.

A thirteenth embodiment of the present invention, as shown in FIG. 25, provides an air-fuel ratio sensor similar to the twelfth embodiment but different in that trapping member 25 is interposed between the bottom of the inside protecting cover 31 and the outside protecting cover 32.

Miscellaneous

According to the above-described embodiments, protecting covers 31 and 32 have flat bottom surfaces. However, it is possible to form each bottom into a curved configuration. Furthermore, the shape of gas hole is not limited to a round shape. For example, it is possible to provide square or rectangular gas holes.

Yet further, the heater unit inserted in the solid electrolyte of the oxygen concentration sensing element is not limited to the stick-like one. Any heater unit, for example, the one disclosed in Japanese Patent No. 5-46498 or a plane heater disclosed in Unexamined Japanese Patent Application No. 5-26842, will be used.

As this invention may be embodied in several forms without departing from the spirit of essential characteristics thereof, the present embodiments as described are therefore intended to be only illustrative and not restrictive, since the scope of the invention is defined by the appended claims rather than by the description preceding them, and all changes that fall within the metes and bounds of the claims, or equivalents of such metes and bounds, are therefore intended to be embraced by the claims.

What is claimed is:

1. An air-fuel ratio sensor, comprising:

an air-fuel ratio sensing element with a solid electrolyte having a detecting portion for detecting a gas concentration of measured gas;

a housing for holding said air-fuel ratio sensing element: and protecting means for covering said detecting portion of said solid electrolyte, said protecting means having gas holes opened for introducing measured gas, wherein said protecting means comprises an inside protecting cover disposed adjacent to said solid electrolyte and an outside protecting cover surrounding said inside protecting cover;

said inside protecting cover is formed into a cup-shaped cylindrical configuration having a closed-end portion at one end and an opened-end portion at the other end, and at least one flange portion protruding outward is formed at said opened-end portion of said inside protecting cover:

said outside protecting cover is formed into a cup-shaped cylindrical configuration having a closed-end portion at one end and an opened-end portion at the other end, and at least one flange portion protruding outward is formed at said opened-end portion of said outside protecting cover;

said flange portion of said inside protecting cover and said flange portion of said outside protecting cover are fixed to said housing by caulking;

said inside protecting cover comprises a plurality of flange portions while said outside protecting cover comprises a plurality of flange portions; and said flange portions of said inside protecting cover and said flange portions of said outside protecting cover are alternately positioned along a same closed curve surrounding an axis of said air-fuel ratio sensing element.

2. The air-fuel ratio sensor in accordance with claim 1, wherein at least one of said inside and outside protecting covers has a gas hole formed on the closed-end portion.

3. The air-fuel ratio sensor in accordance with claim 2, wherein gas holes opened on the closed-end portions of said inside and outside protecting covers are offset from each other, so that said gas holes are not overlapped when projected on a plane parallel to said closed-end portions.

4. The air-fuel ratio sensor in accordance with claim 2, wherein only one gas hole is opened on the closed-end portion of one of said inside and outside protecting covers, while a plurality of gas holes are symmetrically opened on the closed-end portion of the other of said inside and outside protecting covers.

5. The air-fuel ratio sensor in accordance with claim 1, wherein said flange portion of at least one of said inside protecting cover and said outside protecting cover has an undulated surface waving along a closed curve surrounding an axis of said air-fuel ratio sensing element.

6. The air-fuel ratio sensor in accordance with claim 1, wherein a trapping member absorbing water contained in measured gas is interposed between said closed-end portions of said inside and outside protecting covers.

7. An air-fuel ratio sensor, comprising:
   an air-fuel ratio sensing element with a solid electrolyte having a detecting portion for detecting a gas concentration of measured gas;
   a housing for holding said air-fuel ratio sensing element; and
   protecting means for covering said detecting portion of said solid electrolyte, said protecting means having gas holes opened for introducing measured gas, wherein
   said protecting means comprises an inside protecting cover disposed adjacent to said solid electrolyte and an outside protecting cover surrounding said inside protecting cover;
   said inside protecting cover is formed into a cup-shaped cylindrical configuration having a closed-end portion at one end and an opened-end portion at the other end, and at least one flange portion protruding outward is formed at said opened-end portion of said inside protecting cover;
   said outside protecting cover is formed into a cup-shaped cylindrical configuration having a closed-end portion at one end and an opened-end portion at the other end, and at least one flange portion protruding outward is formed at said opened-end portion of said outside protecting cover;
   said flange portion of said inside protecting cover and said flange portion of said outside protecting cover are fixed to said housing by caulking;
   at lease one cutout portion is formed at the opened-end portion of said outside protecting cover, said cutout portion extending in an axial direction of said outside protecting cover;
   an expanded connecting portion is formed at the opened-end portion of said inside protecting cover, said expanded connecting portion is coupled with said cutout portion of said outside protecting cover; and
   said flange portion of said inside protecting cover is connected integrally to a distal end of said expanded connecting portion, so that said flange portion of said inside protecting cover and said flange portion of said outside protecting cover are positioned along a same closed curve when said inside protecting cover is coupled with said outside protecting cover.

8. The air-fuel ratio sensor in accordance with claim 7, wherein a clearance is provided between said expanded connecting portion of said inside protecting cover and said cutout of said outside protecting cover when said inside protecting cover is coupled with said outside protecting cover.

9. The air-fuel ratio sensor in accordance with claim 7, wherein at least one of said inside and outside protecting covers has a gas hole formed on the closed-end portion.

10. The air-fuel ratio sensor in accordance with claim 7, wherein said flange portion of at least one of said inside protecting cover and said outside protecting cover has an undulated surface waving along a closed curve surrounding an axis of said air-fuel ratio sensing element.

11. The air-fuel ratio sensor in accordance with claim 7, wherein a trapping member absorbing water contained in measured gas is interposed between said closed-end portions of said inside and outside protecting covers.

12. An air-fuel ratio sensor, comprising:
   an air-fuel ratio sensing element with a solid electrolyte having a detecting portion for detecting a gas concentration of measured gas;
   a housing for holding said air-fuel ratio sensing element; and
   protecting means for covering said detecting portion of said solid electrolyte, said protecting means having gas holes opened for introducing measured gas, wherein
   said protecting means comprises an inside protecting cover disposed adjacent to said solid electrolyte and an outside protecting cover surrounding said inside protecting cover;
   said inside protecting cover is formed into a cup-shaped cylindrical configuration having a closed-end portion at one end and an opened-end portion at the other end, and at least one flange portion protruding outward is formed at said opened-end portion of said inside protecting cover;
   said outside protecting cover is formed into a cup-shaped cylindrical configuration having a closed-end portion at one end and an opened-end portion at the other end, and at least one flange portion protruding outward is formed at said opened-end portion of said outside protecting cover;
   said flange portion of said inside protecting cover and said flange portion of said outside protecting cover are fixed to said housing by caulking;
   said inside protecting cover comprises a cylindrical barrel portion with a closed-end portion at one end and an opened-end portion at the other end, expanded connecting portions being offset radially outward from the open-end portion of said barrel portion, and flange portions integrally formed with said expanded connecting portions so as to protrude outward; and
   said outside protecting cover comprises a cylindrical barrel portion with a closed-end portion at one end and an opened-end portion at the other end, elongated connecting portions extending along the same surface as said cylindrical barrel portion of said outside protecting cover, and flange portions integrally formed with said elongated connecting portions so as to protrude outward.

13. The air-fuel ratio sensor in accordance with claim 12, wherein said expanded connecting portions of said inside protecting cover and said elongated connecting portions of said outside protecting cover do not overlap with each other when said inside protecting cover is coupled with said outside protecting cover.

14. The air-fuel ratio sensor in accordance with claim 12, wherein said expanded connecting portions of said inside protecting cover and said elongated connecting portions of said outside protecting cover are alternately positioned along a same closed curve surrounding an axis of said air-fuel ratio sensing element when said inside protecting cover is coupled with said outside protecting cover.

15. The air-fuel ratio sensor in accordance with claim 14, wherein gas holes are formed between said expanded connecting portions of said inside protecting cover and said elongated connecting portions of said outside protecting cover.

16. The air-fuel ratio sensor in accordance with claim 12, wherein at least one of said inside and outside protecting covers has a gas hole formed on the closed-end portion.

17. The air-fuel ratio sensor in accordance with claim 12, wherein said flange portion of at least one of said inside protecting cover and said outside protecting cover has an undulated surface waving along a closed curve surrounding an axis of said air-fuel ratio sensing element.

18. The air-fuel ratio sensor in accordance with claim 12, wherein a trapping member absorbing water contained in measured gas is interposed between said closed-end portions of said inside and outside protecting covers.

* * * * *